US006461804B1

(12) United States Patent
Deroover

(10) Patent No.: US 6,461,804 B1
(45) Date of Patent: Oct. 8, 2002

(54) IR-PHOTOGRAPHIC SENSITIZING DYES

(75) Inventor: Geert Deroover, Lier (BE)

(73) Assignee: Agfa-Gevaert, Mortsel (BE)

( * ) Notice: Subject to any disclaimer, the term of this patent is extended or adjusted under 35 U.S.C. 154(b) by 0 days.

(21) Appl. No.: 09/688,368

(22) Filed: Oct. 12, 2000

Related U.S. Application Data

(60) Provisional application No. 60/162,195, filed on Oct. 26, 1999.

(30) Foreign Application Priority Data

Oct. 13, 1999 (EP) ............................................ 99203351

(51) Int. Cl.[7] ............................ G03C 1/20; G03C 5/16; C07D 209/90

(52) U.S. Cl. .................... 430/578; 430/271.1; 430/343; 430/944; 430/964; 548/436

(58) Field of Search ................................ 430/578, 944, 430/964, 343, 271.1; 548/436

(56) References Cited

U.S. PATENT DOCUMENTS

| | | | |
|---|---|---|---|
| 4,876,356 A | 10/1989 | Dust et al. | 430/270 |
| 4,906,541 A | 3/1990 | Dust et al. | 430/49 |
| 5,002,863 A | 3/1991 | Dust et al. | 430/495 |
| 5,405,968 A | 4/1995 | Albert et al. | |
| 5,948,600 A | 9/1999 | Roschger et al. | 430/348 |
| 6,060,218 A * | 5/2000 | Van Damme et al. | 430/944 |

FOREIGN PATENT DOCUMENTS

| | | |
|---|---|---|
| CA | 1237911 | 12/1999 |
| EP | 0 770 497 A1 | 5/1997 |
| JP | 04 194841 A | 7/1992 |

* cited by examiner

*Primary Examiner*—Richard L. Schilling
(74) *Attorney, Agent, or Firm*—Breiner & Breiner, L.L.C.

(57) ABSTRACT

According to the present invention there is provided a class of IR-sensitizing dyes, comprising two benzoindol rings and at least two sulphonic acid groups corresponding to the general formula I:

Formula I

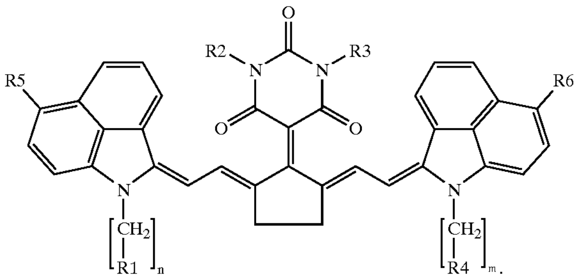

6 Claims, No Drawings

IR-PHOTOGRAPHIC SENSITIZING DYES

RELATED APPLICATION

This application claims benefit of U.S. Provisional Application Serial No. 60/162,195 filed Oct. 29, 1999.

FIELD OF THE INVENTION

The present invention relates to a new type of IR-sensitizing dyes and photographic materials containing these compounds.

BACKGROUND OF THE INVENTION

Light-absorbing dyes incorporated in photographic materials can accomplish a variety of goals, including their use as sensitizing dyes.

In silver halide photographic material these dyes are used as classical sensitizing dyes, preferably in the presence of a supersensitizer. In heat mode photographic materials these dyes are used as compounds capable of converting light into heat.

In recent years new techniques of image recording have emerged wherein the exposure source of the recording apparatus is a laser unit. For instance, one application of lasers as exposure unit is situated in the field of radiographic monitoring photography where a hard copy of radiographic information has to be produced. Other applications are situated in the field of phototype-setting and image-setting, where recorders are marketed which employ Ar ion lasers, He-Ne lasers or solid state semiconductor lasers, also called laserdiodes, as exposure source. The latter type of laser, the laserdiode, shows some advantages compared to other laser types such as low cost price, small size, long life time and no need for an acoustic-optical modulator. Generally the emission wavelength of these semiconductor laser beams is longer than 700 nm and mostly longer than 750 nm. Preferred are laser devices emitting at around 830 and 1060 nm. So, photographic materials appropriate for exposure by devices employing such laser diodes must be sensitized for the near infra-red region of the radiation spectrum.

An infra-red sensitized element must contain an infra-red spectral sensitizer. Compounds suitable as infra-red spectral sensitizer are disclosed in e.g. DE-A- 19 834 745, DE-A- 19 834 746, EP-A- 652 483, DE-A- 4 128 439 and EP-A- 444 786. The disclosed spectral sensitizers are however not optimal for spectral sensitization at 830 and 1060 nm for one or another reason such as no optimal spectral sensitization, a weak conversion of light into heat, rest absorbance, etc. So, there remains a need for better suitable spectral sensitizers.

OBJECTS OF THE INVENTION

It is an object of the present invention to provide spectral sensitizing compounds that are optimally suited for use in materials which would be irradiated with infra-red light emitting lasers.

SUMMARY OF THE INVENTION

According to the present invention there is provided a class of IR-sensitizing dyes, comprising two benzoindol rings and at least two sulphonic acid groups as defined in claim 1.

DETAILED DESCRIPTION OF THE INVENTION

Preferably said IR-sensitizing dyes, comprising two benzoindol rings and at least two sulphonic acid groups corresponding to the general formula I:

(I)

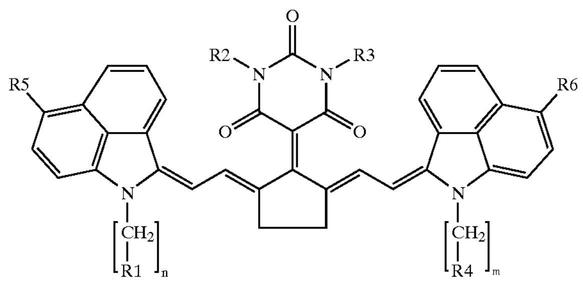

wherein $R_1$ and $R_4$ each independently represent a hydrogen, an alkyl, an aryl or a sulphonic acid group $R_2$ and $R_3$ each independently represent a hydrogen or an alkyl group, $R_5$ and $R_6$ each independently represent a hydrogen, or sulphonic acid group n and m each independently represents an integer from 1 to 6 wherein at least $R_1$ and $R_4$ or $R_5$ and $R_6$ represent a sulphonic acid group.

"More preferably, said IR-sensitizing dyes, comprising two benzoindol rings and at least two sulphonic acid groups, correspond to the general formula I wherein at least $R_5$ and $R_6$ are sulphonic acid groups."

Examples of the IR-sensitizing dyes and their mode of preparation are listed below.

intermediate product 1

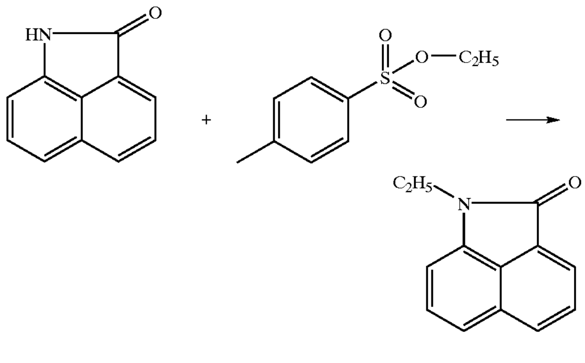

1 mole of product 1 and 1.2 mole of product 2 were dissolved in 300 ml of N-methyl-2-pyrrolidone and warmed till 50° C. 1.2 mol potassium hydroxide was added in 45 min at 50° C. The mixture was then stirred for 30 min at 50° C. and then was added 600 ml of methyl-t-butylether. The mixture was filtered and the filtrate evaporated till dry. The yield was 100%.

intermediate product 2

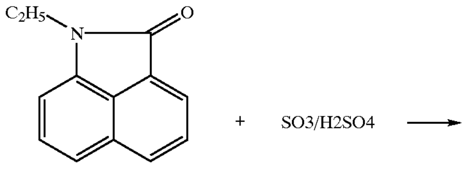

-continued

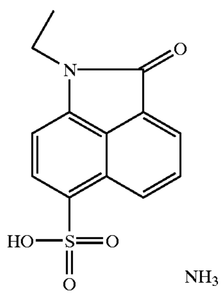

1 mole of intermediate product 1 is added to a mixture of 300 g sulfuric acid and 180 g fuming sulfuric acid. The mixture is let standing for 30 min and then is added concentrated ammonia till weak acid pH. This mixture is cooled to 20° C. and the product is filtered off. Yield 80%.

intermediate product 3

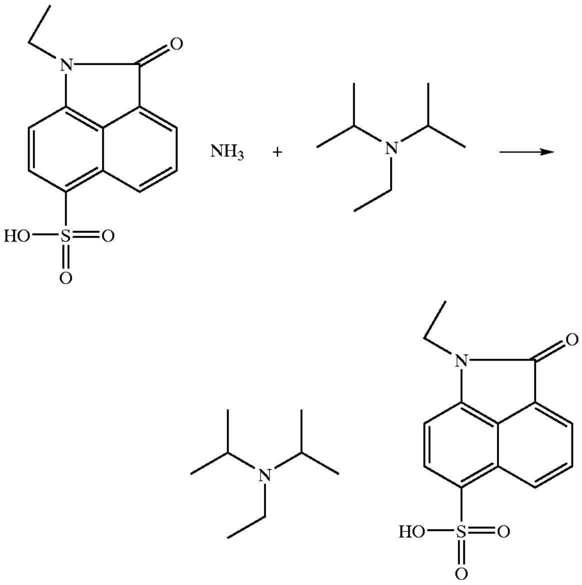

1 mole of intermediate product 2 and 1.5 mole of product 4 is added to 1000 ml i-propanol and warmed till boiling. The mixture is refluxed till almost a solution. The mixture is then cooled and filtered. To the filtrate is added 3000 ml ethylacetate, the mixture is filtered and the solid product is dried. Yield 45%.

intermediate product 4

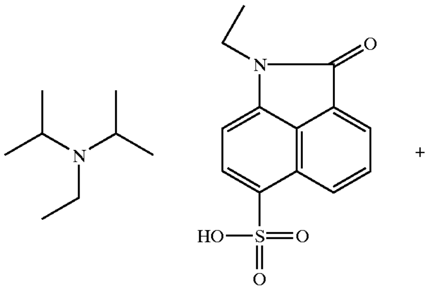

-continued

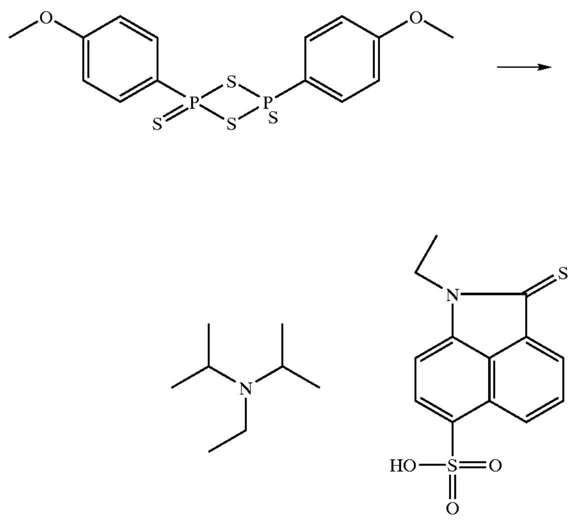

1 mole intermediate product 3 is suspended in 1500 ml methylene chloride and 1500 ml tetrahydrofurane. 0.6 mole of product 5 is added and the mixture is let reacting for 5 h at 40° C. The methylene chloride is then distilled off and replaced by ethylacetate. The mixture is cooled and the precipitation is filtered and dried. Yield 67%.

intermediate product 5

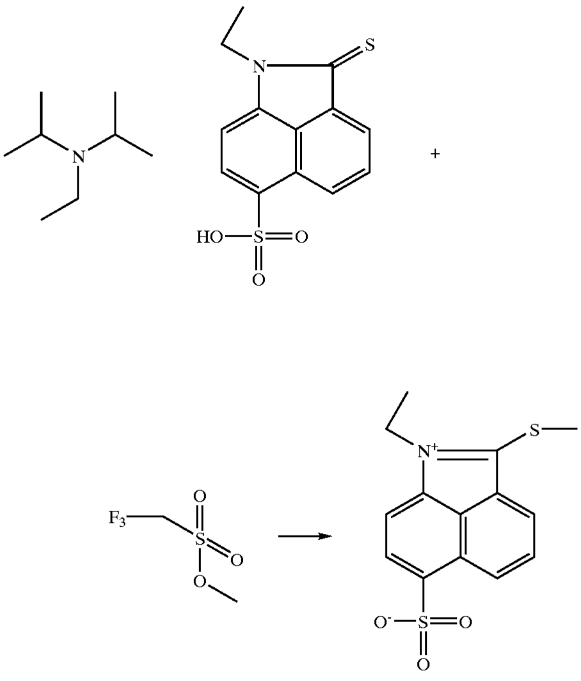

1 mole of intermediate product 4 is dissolved in 1300 ml of methylene chloride. Thereto is added dropwise 1.2 mol of product 6. The mixture is stirred for 30 min. 1300 ml of ethylacetate is added. The solid is filtered off and dried. Yield 87%.

intermediate product 6

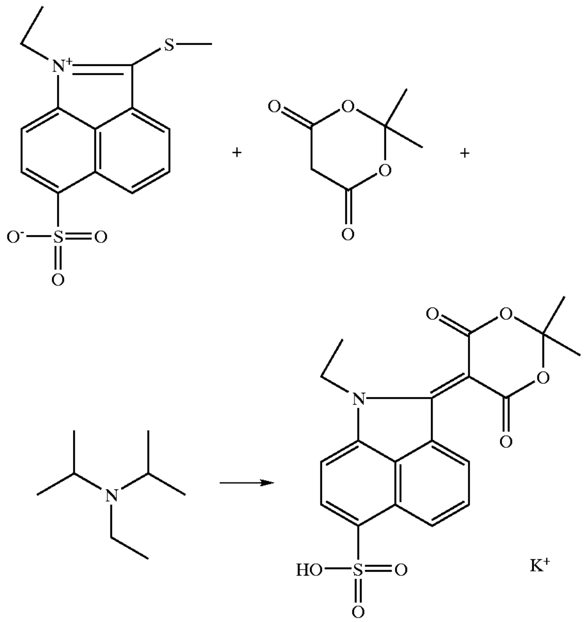

1 mole of intermediate product 5 and 1.5 of product 7 are dissolved in 1700 ml ethanol. 1.5 mole product 4 is added and the mixture is left standing for 2 h at 50° C. 1 mole potassium acetate is added and the mixture is stirred for 1 h at 20° C. The precipitate is filtered off and dried. Yield 40%.

intermediate product 7

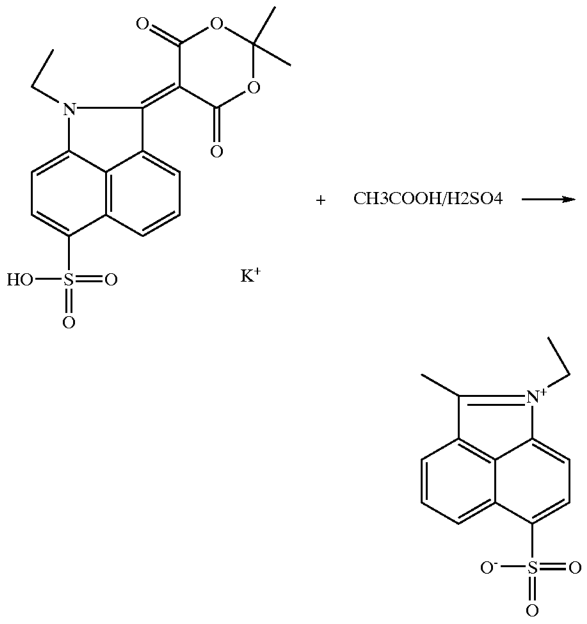

1 mole of product 6 is dissolved in 2600 ml of acetic acid and sulfuric acid is added till the color changes. The mixture is filtered and there is added a mixture of 32000 ml of methyl-t-butylether/ethylacetate 1/1 to the filtrate. After stirring for 30 min the precipitate is filtered off and dried. Yield 36%.

intermediate product 8

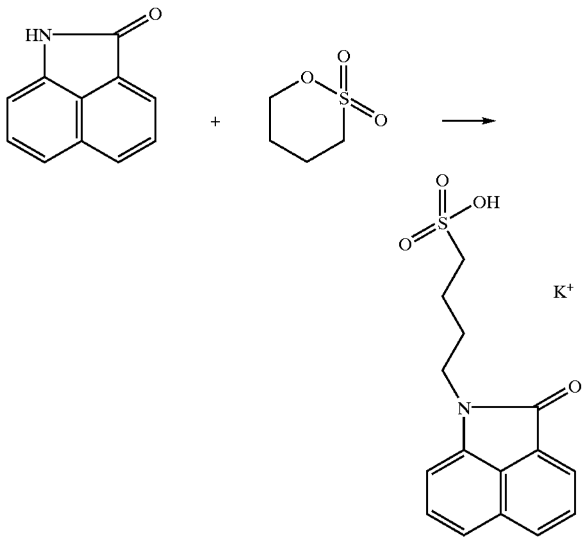

1 mole of product 1 is dissolved in 300 ml N-methyl-2-pyrrolidone. Thereto is added 1.2 mole of product 9 and 1.1 mole of potassium hydroxide. The mixture is heated for 1 h at 80° C. Thereto is added 1000 ml of acetone and cooled. The solid is filtered off and dried. Yield 100%.

intermediate product 9

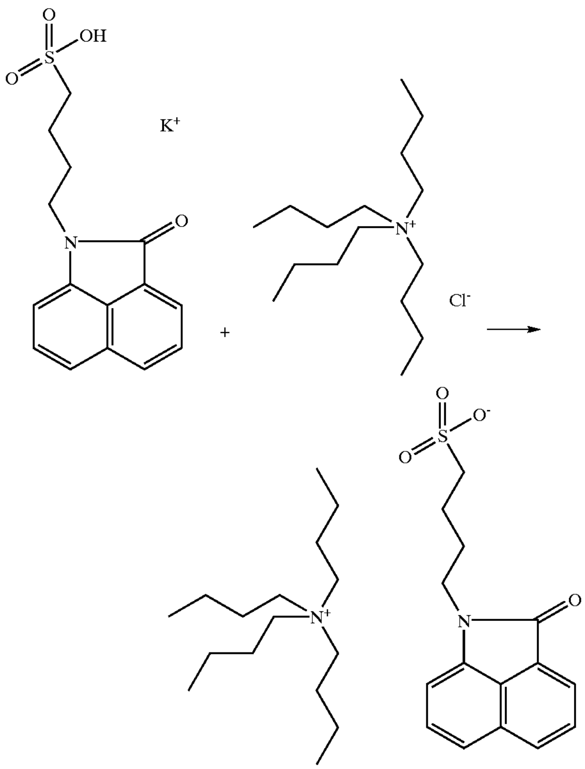

1 mole of intermediate product 8 and 1.05 mole of product 10 are dissolved in 500 ml of acetic acid. The solution is warmed up till 110° C. 1000 ml of ethylacetate is added. The mixture is cooled to 20° C., filtered and the filtrate is evaporated till an oil. To this oil was added 500 ml of toluene and this solution was evaporated till an oil. Yield 100%.

intermediate product 10

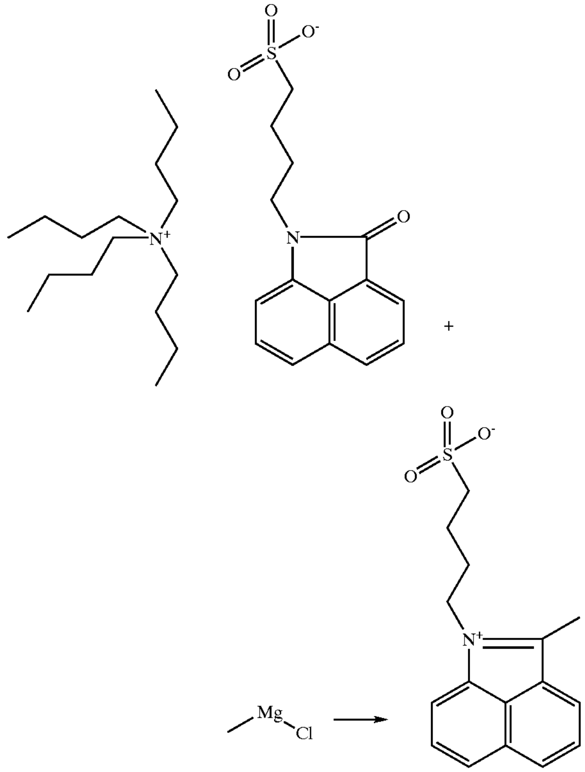

1 mole of intermediate product 9 is dissolved in 4000 ml of tetrahydrofurane and 1500 ml of product 8 (3 mole/l tetrahydrofurane) is added dropwise. The mixture is stirred for 1 h at 60° C. Afterwards the mixture is poured out into 1100 ml concentrated hydrochloric acid and 5000 ml of water. The mixture is concentrated to 1800 g and 2000 ethanol is added. The mixture is chilled for 50 h at 4° C. The precipitate is filtered off and dried. Yield 100%.

intermediate product 11

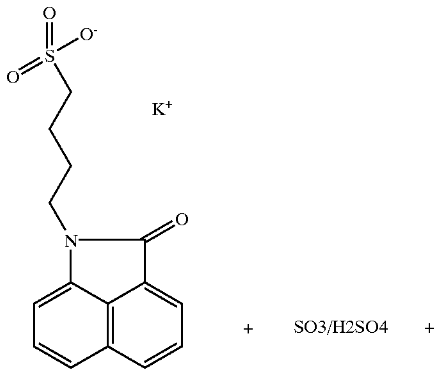

-continued

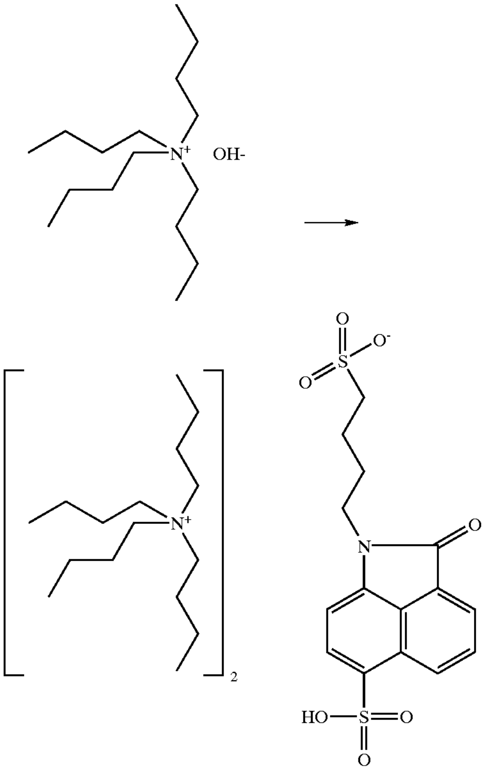

1 mole of intermediate product 8 is added to 320 g of sulfuric acid and 200 gr of fuming sulfuric acid. The mixture is left for 30 min at 60° C. Thereafter 2000 ml of acetic acid and 850 g of ammonium acetate is added and this mixture is warmed for 30 min at 100° C. The mixture is then cooled to 20° C. and filtered. The residue id boiled in acetic acid, filtered and evaporated to dry. 0.18 mole of product 8 is added ( 40% in water), the mixture is boiled for 30 min, filtered and the filtrate evaporated to dry. Toluene is added and the mixture evaporated to an oil. Yield: 6% intermediate product 12

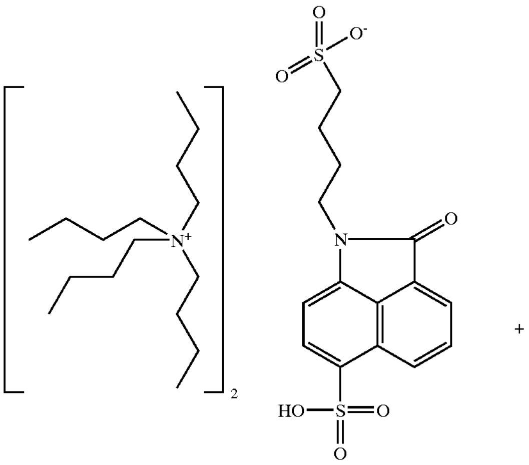

-continued

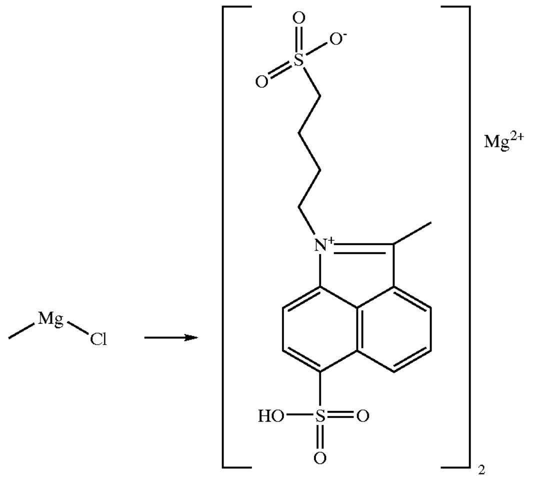

1 mole of intermediate product 11 is dissolved in 5000 ml of tetrahydrofurane and thereto is added 1000 ml of product 8 (3 mol/l in tetrahydrofurane). The mixture is stirred for 30 min at 600° C., poured in 5000 ml methanol with 6 mole of methane sulphonic acid and cooled to 20° C. The residue is filtered of and dried. Yield: 75%.

intermediate product 13

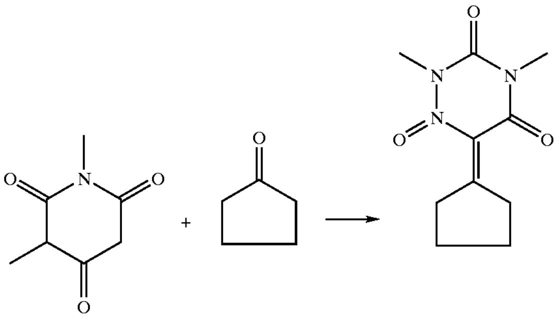

1 mole of product 12, 2 mole of product 13 and 0.02 mole of ammonium acetate are mixed in 350 ml of methanol and refluxed for 90 min. The mixture is cooled, 150 ml of methanol and 50 ml of water are added and the residue is filtered of and dried. Yield: 80%.

intermediate product 14

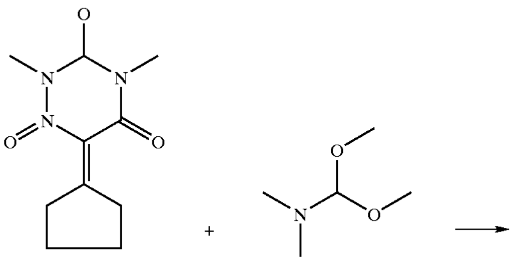

-continued

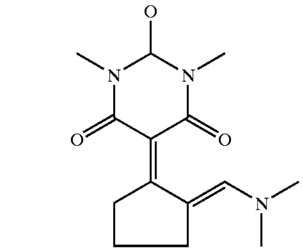

1 mole of intermediate product 13 is added to 1200 ml of toluene. 1 mole of acetic acid is added. 1.1 mole of product 14 is dropped into the mixture and said mixture is stirred for 150 min. The residue is filtered of and dried. Yield: 80% intermediate product 15

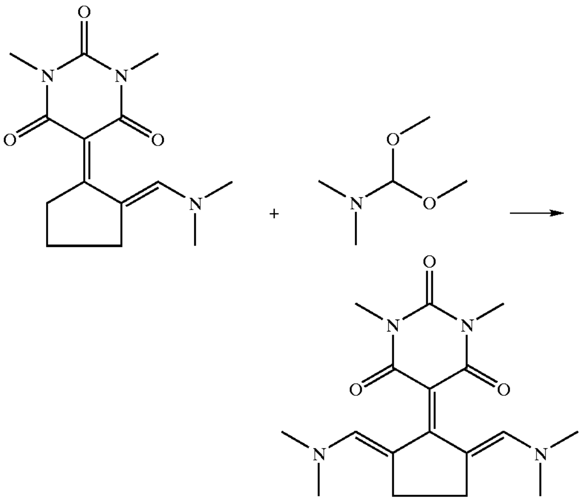

1 mole of intermediate product 14 is brought into 1000 ml of methanol and warmed to reflux. To this mixture is dropped 5 mole of product 14, dissolved in 1000 ml of methanol in 3 hours. The mixture is refluxed for 30 min, cooled to 20° C. and left for 16 hours. The residue is filtered off and dried. Yield: 50% intermediate product 16

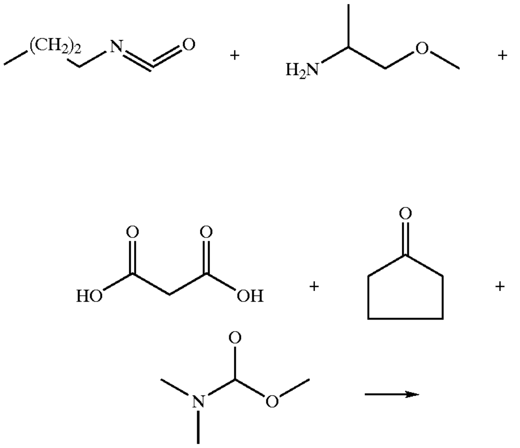

-continued

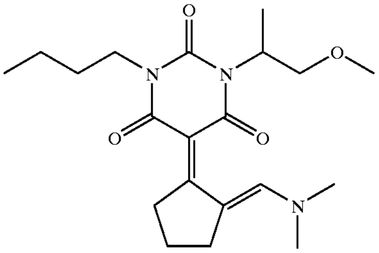

To a mixture of 1.03 mole of product 15 in 70 ml of toluene is dropped 1 mole of product 16 at 50° C. The mixture is stirred for 30 min at 50° C. and the toluene is distilled off. 140 ml of acetic acid is added. To this mixture 1 mole of product 17 and 2 mole of acetic acid anhydride are added and this mixture is warmed at 90° C. for 3 hours. The acetic acid is distilled off and 1.1 mole of product 13, 5 g of ammonium acetate and 100 ml of methanol are added and the mixture is refluxed for 5 hours. The methanol is distilled off the mixture cooled to 20° C. and 400 ml of toluene, 1 mole of acetic acid and 1.15 product 14 are added. 850 ml of hexane is added and the mixture stirred for 30 min. A further 400 ml of hexane is added and the mixture stirred at 20° C. for 1 hour. The residue is filtered off and dried. Yield: 100%.

intermediate product 17

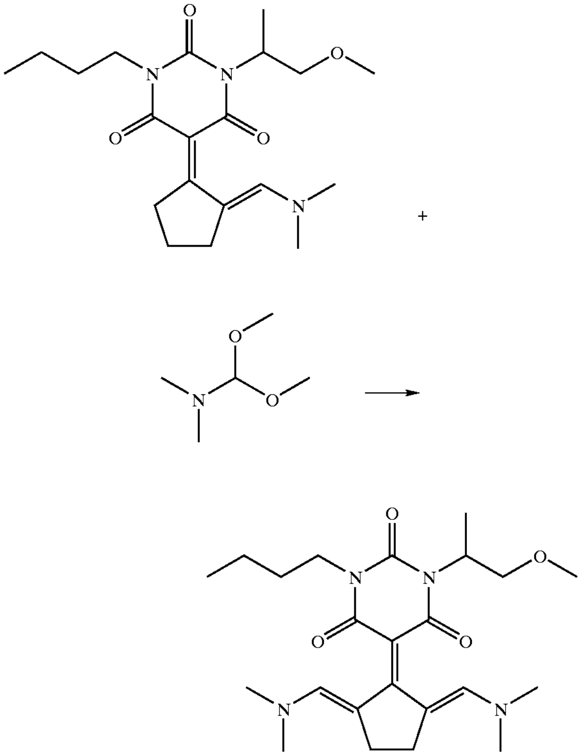

1 mole of intermediate product 16 is dissolved in 320 ml of ethyl acetate and thereto is added 1.15 mole of product 14. The mixture is heated at 65° C. for 30 min. A mixture of 650 ml of methyl t-butyl ether and 150 ml of hexane is added. The mixture is cooled to 20° C., the residue filtered off and dried. Yield: 50%.

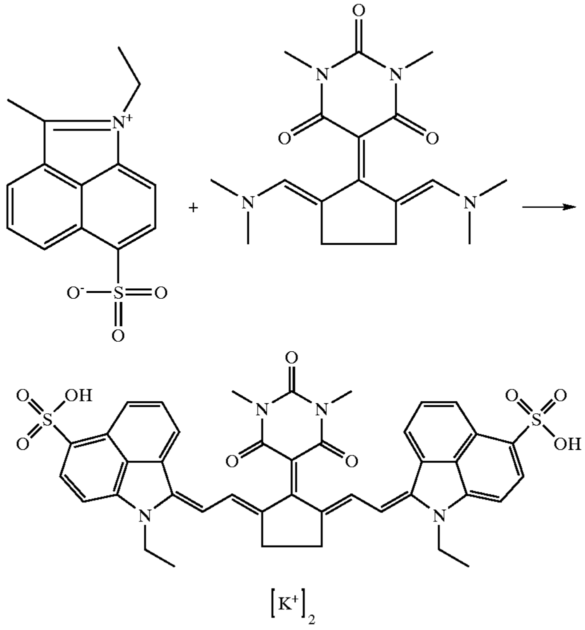

2.2 mole of intermediate product 7 and 1 mole of intermediate product 15 are dissolved in 6000 ml of methanol and the solution is warmed at 60° C. for 30 min. The mixture is poured out in a mixture of 2.5 mole of potassium acetate and 6500 ml of methanol. 13000 ml of ethyl acetate is added, the residue is filtered off and dried. Yield: 80%

Dye 2

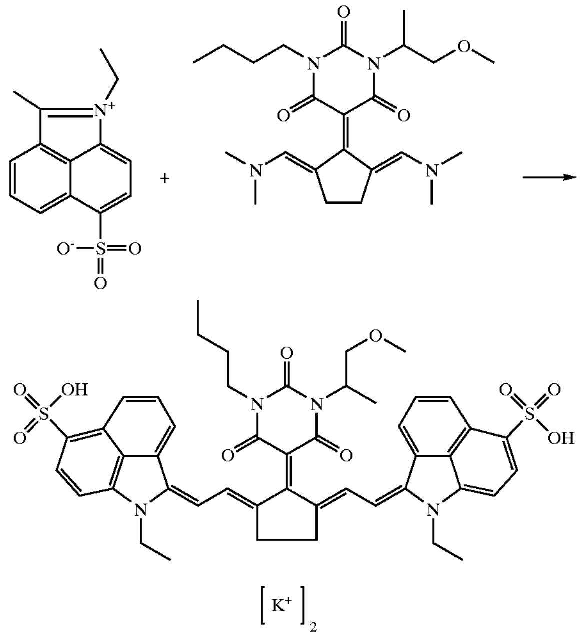

2.2 mole of intermediate product 7 and 1 mole of intermediate product 17 are dissolved in 7000 ml of methanol and the solution is heated for 90 min at 60° C. The mixture is poured out in a mixture of 2.5 mole of potassium acetate and 13000 ml of methanol. The residue is filtered off and dried. Yield: 70%.

Dye 3

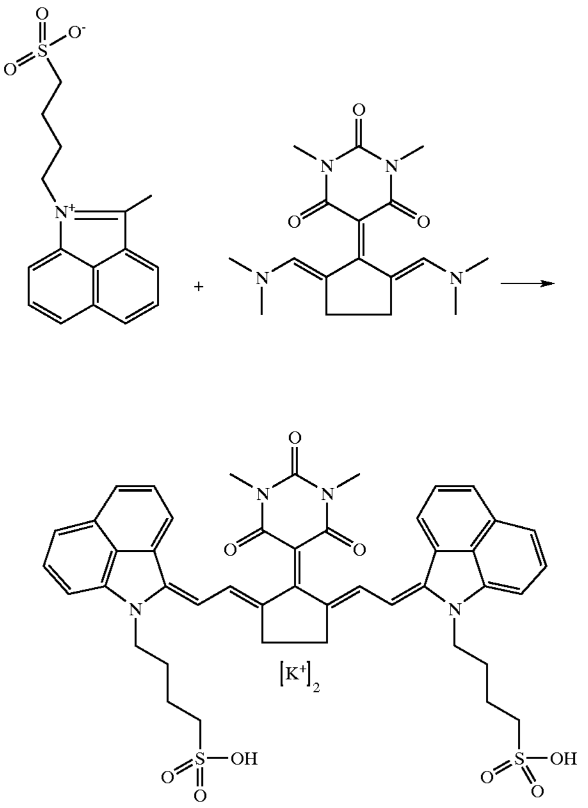

2.2 mole of intermediate product 10 and 1 mole of intermediate product 15 are dissolved in 7000 ml of methanol and stirred for 90 min at 65° C. the solution is cooled to 20° C., filtered and the residue dissolved in 50000 ml of water. 2.2 mole of potassium acetate is added. The product is precipitated by adding 60000 ml of acetone. The residue is filtered off and dried. Yield: 43%.

Dye 4

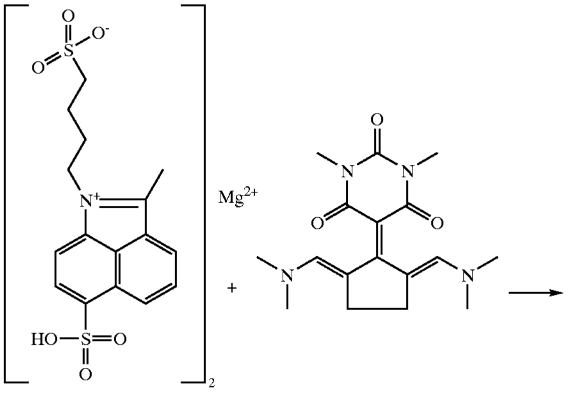

-continued

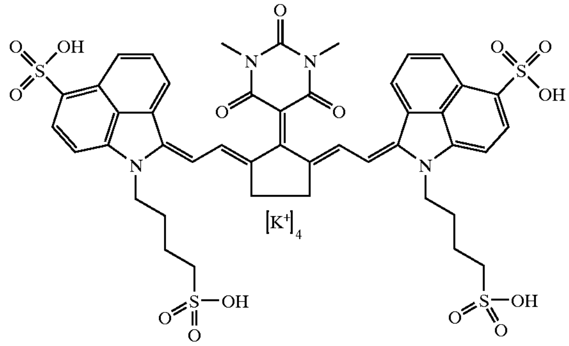

1 mole of intermediate product 12 and 1 mole of intermediate product 15 are dissolved in 7500 ml of methanol and stirred for 1 hour at 55° C. To this solution is added 15000 ml of acetone and the resulting mixture is filtered. The residue is dissolved in a mixture of 30000 ml of methanol and 1500 ml of water, whereto 2.5 mole of potassium acetate is added. To this mixture 30000 ml of acetone is added, the residue is filtered off and dried. Yield: 70%.

These dyes are suitable for classical silver halide emulsion containing materials. They are especially suitable for silver halide emulsion containing materials in the graphical sector.

These dyes are also suitable for thermographic materials, being it silver salt based or non-silver salt based materials. They are very suitable as IR-dye in a heat-sensitive material for making lithographic plates comprising in the order given on a hydrophilic surface of a lithographic base an image forming layer comprising a hydrophilic binder, dispersed hydrophobic thermoplastic polymer particles and a dye according to the invention, which is capable of converting light into heat.

According to the present invention to improve sensitivity and throughput and to avoid scumming an imaging element is provided comprising preferably hydrophobic thermoplastic polymer particles with an average particle size between 40 nm and 2000 nm. More preferably the hydrophobic thermoplastic polymer particles are used with an average particle size of 40 nm to 200 nm. Furthermore the hydrophobic thermoplastic polymer particles used in connection with the present invention preferably have a coagulation temperature above 50° C. and more preferably above 70° C. Coagulation may result from softening or melting of the thermoplastic polymer particles under the influence of heat. There is no specific upper limit to the coagulation temperature of the thermoplastic hydrophobic polymer particles, however the temperature should be sufficiently below the decomposition temperature of the polymer particles. Preferably the coagulation temperature is at least 10° C. below the temperature at which the decomposition of the polymer particles occurs. When said polymer particles are subjected to a temperature above the coagulation temperature they coagulate to form a hydrophobic agglomerate in the hydrophilic layer so that at these parts the hydrophilic layer becomes hydrophobic and oleophilic.

Specific examples of hydrophobic polymer particles for use in connection with the present invention have a Tg above 80° C. Preferably the polymer particles are selected from the group consisting of polyvinyl chloride, polyvinylidene chloride, polyesters, polyurethanes, polyacrylonitrile, polyvinyl carbazole etc., copolymers or mixtures thereof. Most preferably used are polystyrene, polymethylmethacrylate or copolymers thereof.

The weight average molecular weight of the polymers may range from 5,000 to 5,000,000 g/mol.

The polymer particles are present as a dispersion in the aqueous coating liquid of the image-forming layer and may be prepared by the methods disclosed in U.S. Pat. No. 3,476,937. Another method especially suitable for preparing an aqueous dispersion of the thermoplastic polymer particles comprises:

dissolving the hydrophobic thermoplastic polymer in an organic water immiscible solvent, dispersing the thus obtained solution in water or in an aqueous medium and removing the organic solvent by evaporation.

The amount of hydrophobic thermoplastic polymer particles contained in the image-forming layer is preferably between 2 and 40% by weight and more preferably between 10 and 20% by weight of the total weight of said layer.

Suitable hydrophilic binders for use in an image-forming layer in connection with this invention are water soluble (co)polymers for example synthetic homo- or copolymers such as polyvinylalcohol, a poly(meth)acrylic acid, a poly (meth)acrylamide, a polyhydroxy-ethyl(meth)acrylate, a polyvinylmethylether or natural binders such as gelatin, a polysaccharide such as e.g. dextran, pullulan, cellulose, arabic gum, alginic acid, incline or chemically modified inuline.

A light-to-heat converting compound in connection with the present invention is most preferably added to the image-forming layer but at least part of the light-to-heat converting compound may also be comprised in a neighboring layer.

The imaging layer preferably contains surfactants that can be anionic, cationic, non-ionic or amphoteric. Perfluoro surfactants are preferred. Particularly preferred are non-ionic perfluoro surfactants. Said surfactants can be used alone or preferably in combination.

The weight of the imaging layer ranges preferably from 0.5 to 20 $g/m^2$, more preferably from 3 to 15 $g/m^2$.

The lithographic base according to the present invention can be aluminum e.g. electrochemically and/or mechanically grained and anodized aluminum.

According to another mode in connection with the present invention, the lithographic base having a hydrophilic surface comprises a flexible support, such as e.g. paper or plastic film, provided with a cross-linked hydrophilic layer. A particularly suitable cross-linked hydrophilic layer may be obtained from a hydrophilic binder cross-linked with a cross-linking agent such as formaldehyde, glyoxal, polyisocyanate or a hydrolyzed tetra-alkylorthosilicate. The latter is particularly preferred.

As hydrophilic binder there may be used hydrophilic (co)polymers such as for example, homopolymers and copolymers of vinyl alcohol, acrylamide, methylol acrylamide, methylol methacrylamide, acrylate acid, methacrylate acid, hydroxyethyl acrylate, hydroxyethyl methacrylate or maleic anhydride/vinylmethylether copolymers. The hydrophilicity of the (co)polymer or (co)polymer mixture used is preferably the same as or higher than the hydrophilicity of polyvinyl acetate hydrolyzed to at least an extent of 60 percent by weight, preferably 80 percent by weight.

The amount of crosslinking agent, in particular of tetraalkyl orthosilicate, is preferably at least 0.2 parts by weight per part by weight of hydrophilic binder, more preferably between 0.5 and 5 parts by weight, most preferably between 1.0 parts by weight and 3 parts by weight.

A cross-linked hydrophilic layer in a lithographic base used in accordance with the present embodiment preferably also contains substances that increase the mechanical strength and the porosity of the layer. For this purpose colloidal silica may be used. The colloidal silica employed may be in the form of any commercially available water-dispersion of colloidal silica for example having an average particle size up to 40 nm, e.g. 20 nm. In addition inert particles of larger size than the colloidal silica may be added e.g. silica prepared according to Stober as described in J. Colloid and Interface Sci., Vol. 26, 1968, pages 62 to 69 or alumina particles or particles having an average diameter of at least 100 nm which are particles of titanium dioxide or other heavy metal oxides. By incorporating these particles the surface of the cross-linked hydrophilic layer is given a uniform rough texture consisting of microscopic hills and valleys, which serve as storage places for water in background areas.

The thickness of a cross-linked hydrophilic layer in a lithographic base in accordance with this embodiment may vary in the range of 0.2 to 25 $\mu$m and is preferably 1 to 10 $\mu$m.

Particular examples of suitable cross-linked hydrophilic layers for use in accordance with the present invention are disclosed in EP-A-601 240, GB-P-1 419 512, FR-P-2 300 354, U.S. Pat. Nos. 3,971,660, 4,284,705 and EP-A-514 490.

As flexible support of a lithographic base in connection with the present embodiment it is particularly preferred to use a plastic film e.g. substrated polyethylene terephthalate film, substrated polyethylene naphthalate film, cellulose acetate film, polystyrene film, polycarbonate film etc. The plastic film support may be opaque or transparent.

It is particularly preferred to use a polyester film support to which an adhesion improving layer has been provided. Particularly suitable adhesion improving layers for use in accordance with the present invention comprise a hydrophilic binder and colloidal silica as disclosed in EP-A-619 524, EP-A-620 502 and EP-A-619 525. Preferably, the amount of silica in the adhesion improving layer is between 200 mg per m2 and 750 mg per m2. Further, the ratio of silica to hydrophilic binder is preferably more than 1 and the surface area of the colloidal silica is preferably at least 300 m2 per gram, more preferably at least 500 m2 per gram.

In accordance with the present invention the imaging element is image-wise exposed. During said exposure, the exposed areas are converted to hydrophobic and oleophilic areas while the unexposed areas remain hydrophilic.

Said image-forming can be realized by direct thermal recording wherein the thermal transfer is effected by heat radiation, heat conductivity or inductive heat transport. It is believed that on the heated areas the hydrophobic polymer particles coagulate and form a hydrophobic area while on the non-heated areas the hydrophobic polymer particles remain unchanged and said area remains hydrophilic.

Said image-forming can also effected by irradiation with high intensity light. The heat-sensitive material should then comprise a compound capable of converting light into heat.

Image-wise exposure in connection with the present invention is preferably an image-wise scanning exposure involving the use of a laser or L.E.D. Preferably used are lasers that operate in the infrared or near-infrared, i.e.

wavelength range of 700–1500 nm. Most preferred are laser diodes emitting in the near-infrared.

According to the present invention the plate is then ready for printing without an additional development and can be mounted on the printing press. Alternatively, the plate can be developed with water or an aqueous solution before mounting it on a press.

According to a further method, the imaging element is first mounted on the printing cylinder of the printing press and then image-wise exposed directly on the press. Subsequent to exposure, the imaging element is ready for printing.

The printing plate of the present invention can also be used in the printing process as a seamless sleeve printing plate. In this option the printing plate is soldered in a cylindrical form by means of a laser. This cylindrical printing plate which has as diameter the diameter of the print cylinder is slid on the print cylinder instead of mounting a conventional printing plate. More details on sleeves are given in "Grafisch Nieuws", 15, 1995, page 4 to 6.

The following examples illustrate the present invention without limiting it thereto. All parts and percentages are by weight unless otherwise specified.

EXAMPLES 1

Onto an electrochemically grained and anodized aluminum support was coated to a wet coating thickness of 30 $\mu$m a coating solution having the following composition

| | |
|---|---|
| anionic stabilized polystyrene latex (20%) | 93.8 g |
| demineralized water | 576.3 g |
| 1% solution in water of IR-dye 2 | 250.0 g |
| 5% solution in water of polyacrylic acid | 75.0 g |
| 5% solution in water of a surfactant | 5.0 g |

(the polyacrylic acid is Glascol ™ from Ciba Specialty Chem.)

The resulting imaging element was subsequently imaged on a Gerber C42T operating at a scanning speed of 150 rps and a laser output of 6 Watt.

After imaging the plate was mounted on a GTO46 press using K+E 800 ink and Rotamatic as a fountain.

Subsequently the press was started by allowing the print cylinder with the imaging element mounted thereon to rotate. The dampener rollers of the press were then dropped on the imaging element so as to supply dampening liquid to the imaging element and after 10 revolutions of the print cylinder, the ink rollers were dropped to supply ink. After 10 further revolutions clear prints were obtained with no ink uptake in the non-image parts.

EXAMPLE 2

The imaging element of example 1 was exposed on a Gerber C42T operating at 150 rps and a laser output of 7 Watt.

After imaging the plate was processed in a VA-88-N processor using tap water as a developing solution.

Next the plate was mounted on a GTO 46 press using K+E 800 ink and Rotamatic as a fountain. Clear prints were obtained with no ink uptake in the non-image areas.

EXAMPLE 3

An imaging element was prepared as in example 1 except that dye 2 was replaced by IR-dye 4.

The resulting imaging element was subsequently imaged on a Gerber C42T operating at a scanning speed of 150 rps and a laser output of 7 Watt.

After imaging the plate was mounted on a GTO46 press using K+E 800 ink and Rotamatic as a fountain.

Subsequently the press was started by allowing the print cylinder with the imaging element mounted thereon to rotate. The dampener rollers of the press were then dropped on the imaging element so as to supply dampening liquid to the imaging element and after 10 revolutions of the print cylinder, the ink rollers were dropped to supply ink. After 10 further revolutions clear prints were obtained with no ink uptake in the non-image parts.

EXAMPLE 4

An imaging element was prepared as in example 1 except that dye 2 was replaced by IR-dye 5.

The resulting imaging element was subsequently imaged on a Gerber C42T operating at a scanning speed of 150 rps and a laser output of 7 Watt.

After imaging the plate was mounted on a GTO46 press using K+E 800 ink and Rotamatic as a fountain.

Subsequently the press was started by allowing the print cylinder with the imaging element mounted thereon to rotate. The dampener rollers of the press were then dropped on the imaging element so as to supply dampening liquid to the imaging element and after 10 revolutions of the print cylinder, the ink rollers were dropped to supply ink. After 10 further revolutions clear prints were obtained with no ink uptake in the non-image parts.

What is claimed is:

1. A class of IR-sensitizing dyes comprising two benzoindol rings and at least two sulphonic acid groups corresponding to the general formula I:

Formula I

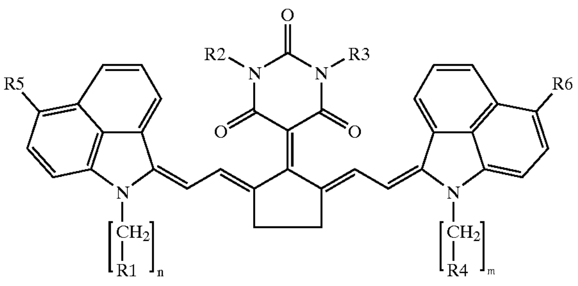

wherein $R_1$ and $R_4$ each independently represent a hydrogen, an alkyl, an aryl or a sulphonic acid group;

$R_2$ and $R_3$ each independently represent a hydrogen or an alkyl group;

$R_5$ and $R_6$ each independently represent a sulphonic acid group;

n and m each independently represents an integer from 1 to 6; and wherein at least $R_1$ and $R_4$ or $R_5$ and $R_6$ represent a sulphonic acid group.

2. A photosensitive material, sensitive for IR light, comprising the IR-sensitive dyes according to claim 1.

3. A photosensitive material according to claim 1 wherein a photosensitive silver halide emulsion is comprised.

4. A thermosensitive material, comprising a compound capable of converting light into heat, wherein said compound capable of converting light into heat is an IR sensitizing dye according to claim 1.

5. A thermosensitive material according to claim 4, wherein said material comprises on a hydrophilic surface of a lithographic base a thermosensitive layer hydrophobic thermoplastic polymer particles, a hydrophilic binder and a compound capable of converting light into heat, wherein said compound capable of converting light into heat is an IR-sensitive dye according to claim 1.

6. A class of IR-sensitizing dyes comprising two benzoindol rings and at least two sulphonic acid groups corresponding to the general formula I:

Formula I

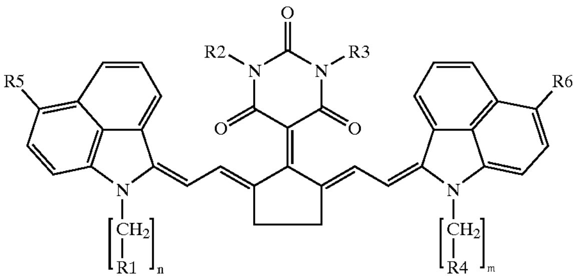

wherein $R_1$ and $R_4$ each independently represent a hydrogen, an alkyl, an aryl or a sulphonic acid group;

$R_2$ and $R_3$ each independently represent a hydrogen or an alkyl group;

$R_5$ and $R_6$ each independently represent a hydrogen, or sulphonic acid group;

n and m each independently represents an integer from 1 to 6; and wherein at least $R_1$ and $R_4$ or $R_5$ and $R_6$ represent a sulphonic acid group, and a photosensitive silver halide emulsion is comprised.

* * * * *

UNITED STATES PATENT AND TRADEMARK OFFICE
CERTIFICATE OF CORRECTION

PATENT NO. : 6,461,804 B1
DATED : October 8, 2002
INVENTOR(S) : Geert Deroover

It is certified that error appears in the above-identified patent and that said Letters Patent is hereby corrected as shown below:

Title page,
Item [60], "Provisional application No. 60/162,195, filed on Oct. 26, 1999." should read -- [60] Provisional application No. 60/162,195, filed on Oct. 29, 1999. --.

Column 9,
Line 26, "600° C." should read -- 60° C." --.

Column 11,
Line 23, "off the mixture" should read -- off, the mixture --.

Column 15,
Line 32, "incline" should read -- inuline --.

Signed and Sealed this

Twenty-eighth Day of January, 2003

JAMES E. ROGAN
*Director of the United States Patent and Trademark Office*